(12) United States Patent
Halldorsson et al.

(10) Patent No.: US 7,774,036 B2
(45) Date of Patent: Aug. 10, 2010

(54) AUTOMATIC REGISTRATION OF IMAGES

(75) Inventors: Gisli Hreinn Halldorsson, Reykjavik (IS); Einar Stefansson, Reykjavik (IS); Jon Atli Benediktsson, Reykjavik (IS); Robert Arnar Karlsson, Reykjavik (IS); Sveinn Hakon Hardarson, Reykjavik (IS); Thor Eysteinsson, Reykjavik (IS); James M. Beach, Slidell, LA (US)

(73) Assignee: Oxymap EHF, Reykjavik (IS)

( * ) Notice: Subject to any disclaimer, the term of this patent is extended or adjusted under 35 U.S.C. 154(b) by 1437 days.

(21) Appl. No.: 11/146,278

(22) Filed: Jun. 7, 2005

(65) Prior Publication Data

US 2006/0276698 A1    Dec. 7, 2006

(51) Int. Cl.
*A61B 5/1455* (2006.01)
(52) U.S. Cl. ..................................... 600/323
(58) Field of Classification Search ................. 382/128, 382/130, 131; 600/323, 478, 425, 476
See application file for complete search history.

(56) References Cited

U.S. PATENT DOCUMENTS

| | | | | |
|---|---|---|---|---|
| 6,053,865 | A * | 4/2000 | Sugiyama et al. | 600/300 |
| 6,198,532 | B1 * | 3/2001 | Cabib et al. | 356/456 |
| 6,569,104 | B2 * | 5/2003 | Ono et al. | 600/504 |
| 6,728,561 | B2 | 4/2004 | Smith et al. | |

FOREIGN PATENT DOCUMENTS

WO    WO/00/06017    *    2/2000

OTHER PUBLICATIONS

Zana et al. , A Multimodal Registration Algorithm of Eye Fundus Images Using Using Vessels Detection and Hough Transform, May 5, 1999, IEEE Transactions on Medical Imaging, vol. 18, No. 5.*
Ashman, Ross A., et al., Oximetry with a multiple wavelength SLO, (2001), International Ophthalmology, vol. 23, pp. 343-346.
Beach, J.M., et al., Oximetry of retinal vessels by dual-wavelength imaging: calibration and influence of pigmentation, (1999), J. Appl Physiol, vol. 86, No. 2, pp. 748-758.
Beach, Jim, Spectral Reflectance Technique for Retinal Blood Oxygen Evaluation in Humans, (2002), IEEE.
Bouzas, Evrydiki A., et al., Distribution and Regulation of the Optic Nerve Head Tissue $PO_2$, Nov. 1997, Surve of Ophthalmology, vol. 42, Supplement 1, pp. 27-34.

(Continued)

*Primary Examiner*—Eric F Winakur
*Assistant Examiner*—Ahmed Elhassan
(74) *Attorney, Agent, or Firm*—Harness, Dickey & Pierce, P.L.C.

(57) ABSTRACT

The example embodiments relate to a system for automatically evaluating oxygen saturation of the optic nerve and retina, including an image capturing system which includes a fundus camera, a four wavelengths beam splitter, a digital image capturing device, a computer system, and image processing software for registering and analyzing multi-spectral images of the retina, and for evaluating oxygen saturation level.

12 Claims, 7 Drawing Sheets

OTHER PUBLICATIONS

Crittin, Mireille et al., Hemoglobin oxygen saturation ($So_2$) in the human ocular fundus measured by reflectance oximetry: preliminary data in retinal veins, (2002), Klin Monatsbi Augenheilkd, vol. 219, No. 4, pp. 289-291.

Chen, Yixin et al., Support Vector Learning for Fuzzy Rule-Based Classification Systems, Dec. 2003, IEEE Transactions on Fuzzy Systems. vol. 11, No. 6, pp. 716-728.

Delaey, Christophe et al., Regulatory Mechanisms in the Retinal and Choroidal Circulation, (2000), Ophthalmic Res, vol. 32, pp. 246-256.

Delori, Francois C., Noninvasive technique for oximetry of blood in retinal vessels, Mar. 15, 1988, Applied Optics, vol. 27, No. 6, pp. 1113-1125.

Halldorsson, Gisli H. et al., Automatic Registration of Spectrophotometric Retinal Images, Jun. 9-11, 2004, IEEE Nordic Signal Processing Workshop (NORSIG 2004), pp. 5-8.

Harris, Alon et al., A Review of Methods for Human Retinal Oximetry, Mar./Apr. 2003, Ophthalmic Surg Lasers Imaging, vol. 34, No. 2, pp. 152-164.

Karlsson, R.A. et al., Automatic selection of measurement points in multispectral fundus images for retinal oximetry, (2004), Invest Ophthalmol, vol. 45, E-abstract 3016.

Meyer, F., Contrast Features Extraction, in Quantitative Analysis of Microstructures in Material Sciences, Biology and Medicine (J.-L. Chermant, ed.), (Stuttgard, FRG), Riederer Verlag, (1978), Special Issue of Practical Metallography, pp. 374-380.

Tiedeman, James, S. et al., Retinal Oxygen Consumption during Hyperglycemia in Patients with Diabetes without Retinopathy, Jan. 1998, Ophthalmology, vol. 105, No. 1, pp. 31-36.

\* cited by examiner

AUTOMATIC REGISTRATION OF IMAGES

TECHNICAL FIELD

The present invention relates to the field of image processing, more particularly to the automatic registration of multi-spectral images. The present invention, moreover, relates to the application of image processing in the field of ophthalmology for spectral, spatial and temporal analysis.

BACKGROUND ART

Some of the disease states that pose the greatest danger to vision are thought to involve abnormalities in the oxygen supply to the retina or the oxygen metabolism. These include diseases such as diabetic retinopathy, which is one of the most common causes of blindness in the world and retinopathy of prematurity, retinal vein and artery occlusions. It has also been suggested that ocular blood flow is compromised in glaucoma, including normal tension glaucoma, and that the loss of optic nerve fibers in glaucoma patients may be due to ischemia.

The principle of spectrophotometric hemoglobin oximetry is old and the method has been developed into clinically useful instrumentation in several specialties of medicine. The finger or earlobe oximeter, commonly used in anesthesiology and intensive care is an example of the successful application of oximetry in medicine.

Information on retinal and optic nerve oxygenation in health and disease is mostly derived from animal research. Non-invasive measurement of oxygenation in the human retina and optic nerve has proved difficult but considerable progress has been made, particularly in recent years as digital technology has evolved. The potential use of retinal oximetry covers a range of areas, including assessment of oxygen metabolism in disease, the efficacy of treatment of these diseases in restoring or improving the metabolic conditions, either by laser treatment, surgery, lowering of intraocular pressure or by medication. Retinal oximetry may also be of use in elucidating further the physiological processes involved in disease states, such as in glaucoma.

Figure 1:
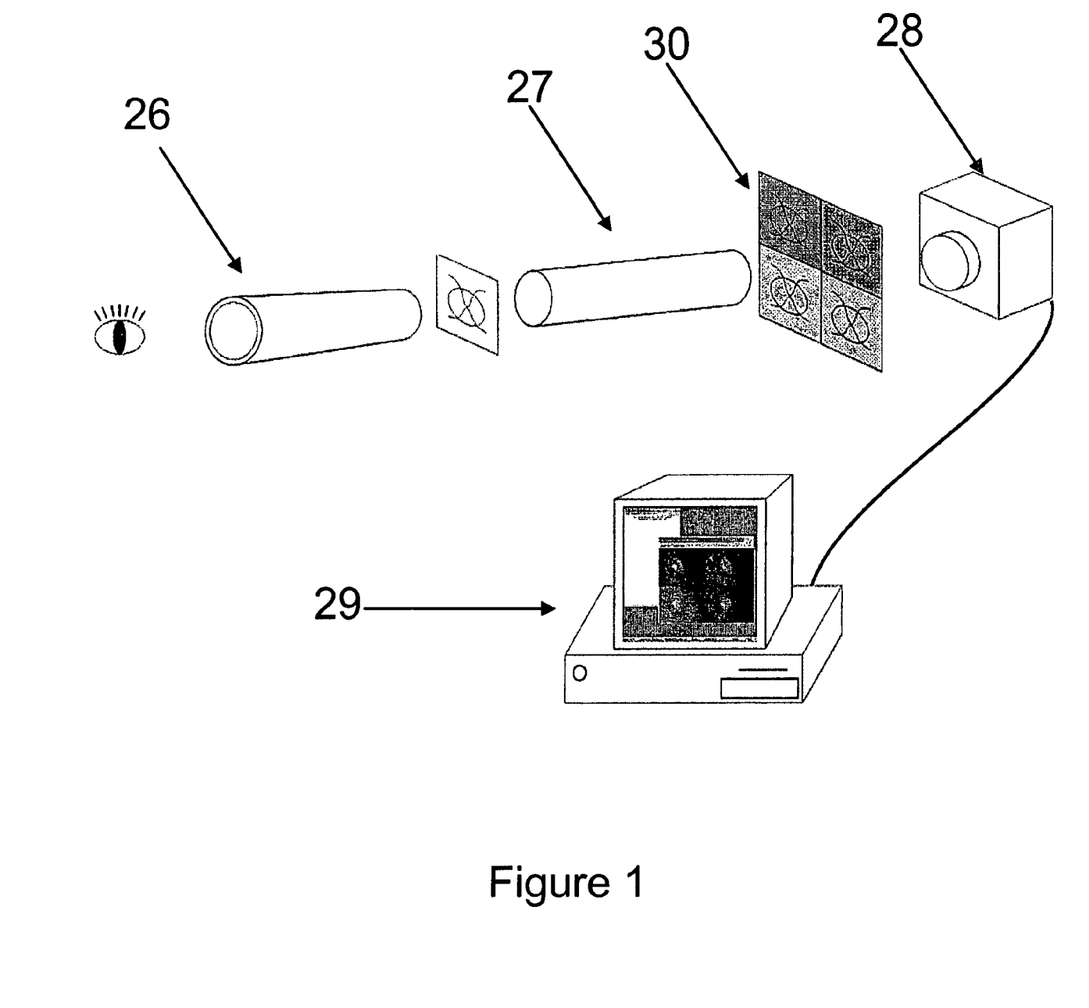
FIG. 1 shows multi-spectral image capturing system.

In the 1990s, an important version of retinal vessel oximetry was developed at the University of Virginia, by James Beach and James Tiedeman [1, 2]. Their version was based on a method proposed by Delori [3] with additional improvements. The main advantage of the Beach and Tiedeman method is the ability to obtain simultaneously two or more images of light reflectance at different wavelengths (called multi-spectral images) from the same fundus using a fundus camera. In this manner it is possible to record reflectance at both oxygen-sensitive and insensitive wavelengths from exactly the same area on the fundus, and at precisely the same time. This allows for precise quantification of the effects of oxygen binding on the light absorption spectra of hemoglobin. Oximetric measurements of this kind are achieved by a system whose main component consists of a modified fundus camera, although the internal xenon flash of the camera is still used as a light source, unmodified. Other components of the system are a beam splitter, a gray scale digital camera, possessing high quality linear performance, and a computer. The digital camera replaces the image acquisition mechanism of the fundus camera. Flashes from the fundus camera are synchronized with recordings by the digital camera electronically. The image thus obtained with the digital camera is then fed into a computer for further analysis. Between the fundus camera and the digital camera there are image-splitting optics, which can project several separate images at the digital camera detector, as illustrated by FIG. 1.

Figure 2:
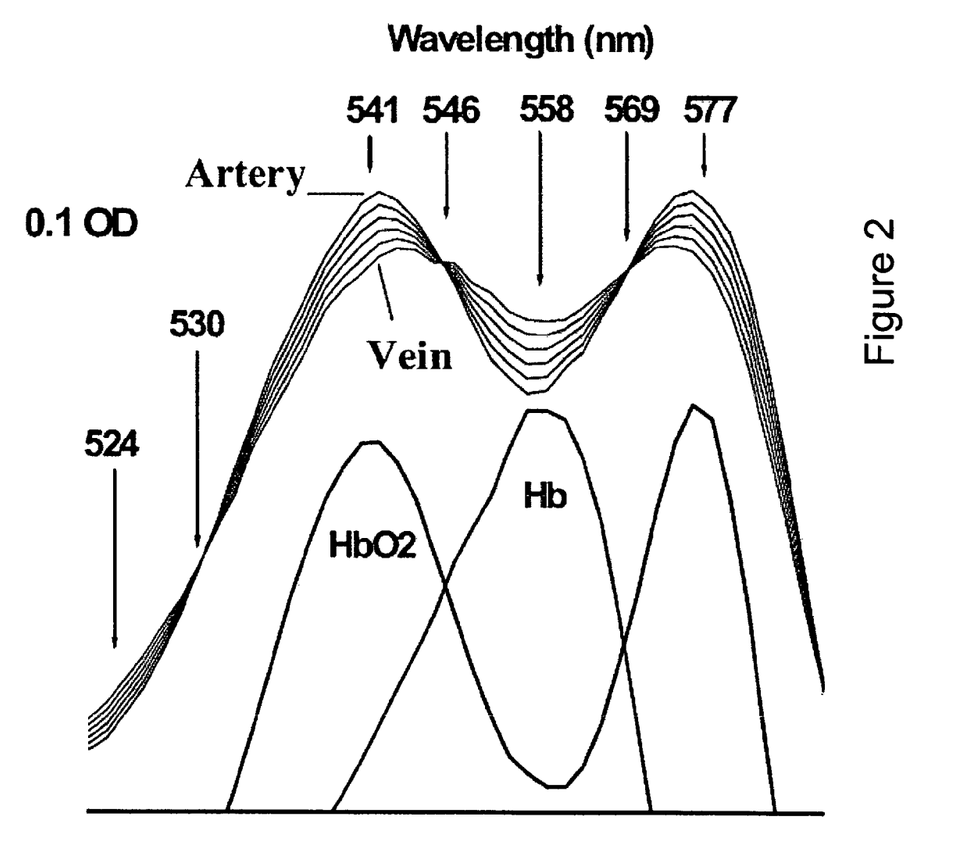
FIG. 2 shows the absorption spectra of the oxyhemoglobin.

In each of these optical pathways, which are separated by a beam splitter and dichroic mirrors, there is a narrow band pass interference filter. Each filter has a 5 nm half-bandwidth and different central (peak) wavelengths of transmission. The filters, or rather their peak wavelengths, are chosen on the basis of the absorption spectra of oxyhemoglobin ($HbO_2$) as before, and illustrated in FIG. 2. The filter bandwidth clearly affects measurements of the blood Optical Density (OD) and this can be evaluated by calculating the apparent light extinction coefficients of $HbO_2$ and hemoglobulin with no oxygen (Hb) [2]. The extinction coefficients are nearly identical at the isosbestic wavelength of 586 nm, particularly at a narrow bandwidth, while considerably higher for Hb than $HbO_2$ at the oxygen-sensitive wavelength (600 or 605 nm). Thus, the apparent Optical Density Ratio (ODR) between the oxygen-sensitive and isosbestic wavelengths reflects the oxygen saturation in retinal vessels and tissue in an inverse manner. With higher oxygen saturation the OD at 605 nm is lower.

OD is a measure of absorption; higher OD means greater absorption [5]. One factor that affects the optical density measured in fundus oximetry is the extravascular pigmentation of the fundus, which can vary greatly between subjects. Pigmentation may cause underestimation of ODs in vessels, in particular at 586 nm, because it causes stronger absorption of light. The effect of retinal pigmentation can be estimated by measuring the ratio of extravascular light reflection near vessels at the oxygen-sensitive and insensitive wavelengths used [2]. The extravascular light reflection ratio (EVR) is calculated as:

$$EVR = \frac{I_{586}}{\eta I_{605}}$$

Where $I_{586}$ is the intensity of 586 nm wave length light reflected, $I_{605}$ is the intensity of 605 nm wave length light reflected, and $\eta$ is a correction constant for light transmission through the instrument (evaluated separately), from the light source to the digital camera, via the beam splitter and optics. Experimentally it has been found that EVR is greater with higher fundus pigmentation [2]. In order to calculate vessel OD it is therefore necessary to correct for pigmentation by measuring intensity at both wavelengths in non-vascular areas.

One of the limitations of prior art retinal oximetry [13] includes difficulties in obtaining calibrated measures of actual oxygen saturation. An indirect calibration of the ODR, as it relates to actual oxygen saturation of vascular blood can be obtained by comparing the ODR and systemic $O_2$ saturation, the latter controlled by having subjects inhale air mixtures of different composition, with 100% oxygen and lower. The reliability of this approach can be further enhanced by measuring the systemic $O_2$ saturation with a finger pulse oximeter. It has been found experimentally in this manner that there is a fairly good inverse correlation between systemic $O_2$ saturation and the ODR (lower ODR with higher systemic $O_2$) in retinal arterioles [2], and venules [4] in normal human volunteers.

Clearly, examination of images of the fundus is an important diagnostic tool in ophthalmology. Fundus images allow inspection of arteries and veins that are usually hidden beneath the skin. Consequently, fundus images may be used to diagnose many diseases that affect the vascular structure.

The problems with the prior art methods used in retinal oximetry is the need for an expert to perform the oximetry, the high variability of the results, and poor reproducibility. The prior art methods are time consuming, and manual registration of the spectral images is inaccurate because of the error prone manual selection of sample points.

DISCLOSURE OF THE INVENTION

The present invention concerns methods, software, and a system that enables in real time the automatic analysis of spectrophotometric measurements of oxygen saturation in the retinal vasculature. The invention enables any number of spectral images to be examined in the same coordinate system, which means that optical density ratios are more reliably and easily obtained. The method is suitable for measuring large part of the fundus at once. The current invention, moreover, automatically finds vessels in the spectral images and calculates the optical density ratios automatically. This has never been done before and results in more reliable measurements than when measurement points are chosen by hand, and can be done automatically and extended by a novice operator.

Terminology Used in the Present Context:

Registering, refers to the process of aligning the spectral images into one coordinate system.

Multi spectral image, refers to multiple images of the same scene acquired at different wavelengths.

Spectral image, is an image acquired at a specific wavelength.

Binarize, refers to the process of reducing the resolution of a gray scale image to black and white only.

Defective pixels, refers to pixels that contain invalid pixel values.

Edge detection, refers to the process of extracting edges or boundaries between two regions in an image.

Top-hat transform, refers to image morphological operator first presented by F. Meyer[12].

Structuring element, refers to a two dimensional matrix of pixel values 0 or 1 describing the neighborhood of an image operator.

Skeletonizing, refers to the process of generating a stick figure representation of the objects in the image being processed.

Prune, refers to the process of removing spurious lines in the image.

Re-Grow, refers to the process of expanding the skeletonized objects to original size.

Vessel map, refers to a map of the vessels in the image.

Vessel profile, refers to the side view of the vessels in the image.

Real-Time, refers to the processing of images on-line without noticeable delay to the human operator.

Isobestic, is by definition a wavelength which is absorbed equally by an oxygenated and deoxygenated hemoglobin solution.

In a one aspect the present invention relates to a method for evaluating oxygen saturation of the optic nerve and retina, said method comprising the steps of: registering set of multi-spectral images (1), locating blood vessels (2) in each of the multi-spectral images, evaluating the width of the blood vessels (3), selecting samples for calculating optical density, calculating the optical density ratio (4), where the optical density is the logarithm of the light reflected from background divided by light reflected from vessel and said optical density ratio is the ratio of said optical density at two different wavelengths, evaluating oxygen saturation level (5), and presenting the results (6), wherein presenting the results may include presenting numerical and visual representation of the oxygen saturation.

In another aspect the present invention relates to a method for automatic registration of multi-spectral images, said method comprises the steps of: binarize the multi-spectral image (7), find the all the border regions of each image, by, finding the region including the straight line that passes the most number of points in the region (8), use the orientation of the borders to evaluate the orientation of each spectral image (9), equalize the orientation of each spectral image by rotating the spectral image (10), edge detect each spectral image (11), estimate the translation between the spectral images based on the edges of adjacent images (12), transform the images to a stack of registered images (13), wherein the images are transformed based on orientation and position of each spectral image.

In another aspect the current invention relates to a method for detecting blood vessels in multi-spectral images, said method comprises the steps of: retrieving registered spectral images (14), for each spectral image, remove defective pixels (15), enhance image contrast (16), perform top-hat transform using structuring element larger than the largest vessel diameter (17), binarize each image (18), apply filter for smoothing the image (19), combine all the spectral images using binary AND operator (20), skeletonize the resulting image (21), prune the skeleton image (22), re-grow the pruned image (23), locate junction points (24), wherein the junction points are the intersection of two or more vessels.

In another aspect the current invention relates to a method for evaluating the width of the blood vessels, said method comprises the steps of: evaluating binary vessel map by calculating the normal vector to the vessel direction to, estimate the direction and position of the vessel profile, evaluate positions of vessel walls based on the vessel profile obtained, evaluate vessel width based on the position of the vessel walls, wherein the width is the distance between the vessel walls.

In another aspect the current invention relates to a method for selecting sample points for optical density calculation, said method comprising the steps of: obtaining a binary vessel map, obtaining vessel profile, locating the points of the vessel profile which have the lowest magnitude, wherein the selected points will provide samples with the least error contributed from the specular reflection of the vessel walls.

In another aspect the present invention relates to computer software realizing a method for evaluating oxygen saturation of the optic nerve and retina.

In another aspect the present invention relates to computer software realizing a method for automatic registration of multi-spectral images.

In another aspect the present invention relates to computer software realizing a method for detecting blood vessels in multi-spectral images.

In another aspect the present invention relates to computer software realizing a method for evaluating the width of blood vessels in multi-spectral images.

In another aspect the present invention relates to computer software realizing a method for selecting sample points for optical density calculation in multi-spectral images.

In another aspect the present invention relates to a system for automatically evaluating oxygen metabolism of the optic nerve and retina, said system comprising: image capturing system further comprising: a fundus camera (26), a four wavelengths beam splitter (27), a digital image capturing device (28), a computer system, image processing software performing in real-time the steps of: registering set of multi-spectral images (1) by, binarizing the multi-spectral image (7), find the all the border regions of each image by finding the region including the straight line that passes the most number of points in the region (8), use the orientation of the borders to evaluate the orientation of each spectral image (9), equalize the orientation of each spectral image by rotating the spectral image (10), edge detect each spectral image (11), estimate the translation between the spectral images based on the edges of adjacent images (12), transform the images to a stack of registered images (13), locating blood vessels (2) in each of the multi-spectral images by, retrieving registered spectral images (14), for each spectral image, remove defective pixels (15), enhance image contrast (16), perform top-hat transform using structuring element larger than the largest vessel diameter (17), binarize each image (18), apply filter for smoothing the image (19), combine all the spectral images using binary AND operator (20), skeletonize the resulting image (21), prune the skeleton image (22), re-grow the pruned image (23), locate junction points (24), evaluating the width of the blood vessels (3) by calculating the normal vector to the vessel direction to, estimate the direction and position of the vessel profile, evaluate positions of vessel walls based on the vessel profile obtained, evaluate vessel width based on the position of the vessel walls, selecting samples for calculating optical density, calculating the optical density ratio (4), evaluating oxygen saturation level (5), and presenting the results (6), wherein presenting the results may include presenting numerical and visual representation of the oxygen saturation.

BEST MODE FOR CARRYING OUT THE INVENTION

The retinal oxymetry process utilizes the fact that the amount of light absorbed by hemoglobin is dependent on the wavelength of the light and the oxygen saturation of the blood. To estimate the amount of light reflected, multi-spectral images containing sub-images at different wavelengths are acquired.

Therefore, the image from the digital camera is a multi-spectral image consisting of 2 or more sub-images. Each sub-image has been filtered with an optical narrow band-pass filter (with center wavelengths 542 nm, 558 nm, 586 nm, and 605 nm). The sub-images, here after referred to as spectral images, represent the same area of the retina. However, an accurate spectral image position and rotation on the multi-spectral image is not known because of the sensitivity of the beam splitter. For this reason, the spectral images may overlap and sometimes parts of the spectral images are outside of the multi-spectral image and therefore parts of the spectral image are missing.

To enable analysis of the retinal oximetry the spectral images have to go through a preprocessing stage were they are pair-wise registered together. The registration process is necessary in order to be able to compute the information extracted from the images in the same coordinate system. The registration algorithm is implemented in the software. The algorithm has been shown to be accurate (mean registration error between two images $\leq 1$ pixel) and computationally inexpensive [7]

Software Specifications

Figure 3:
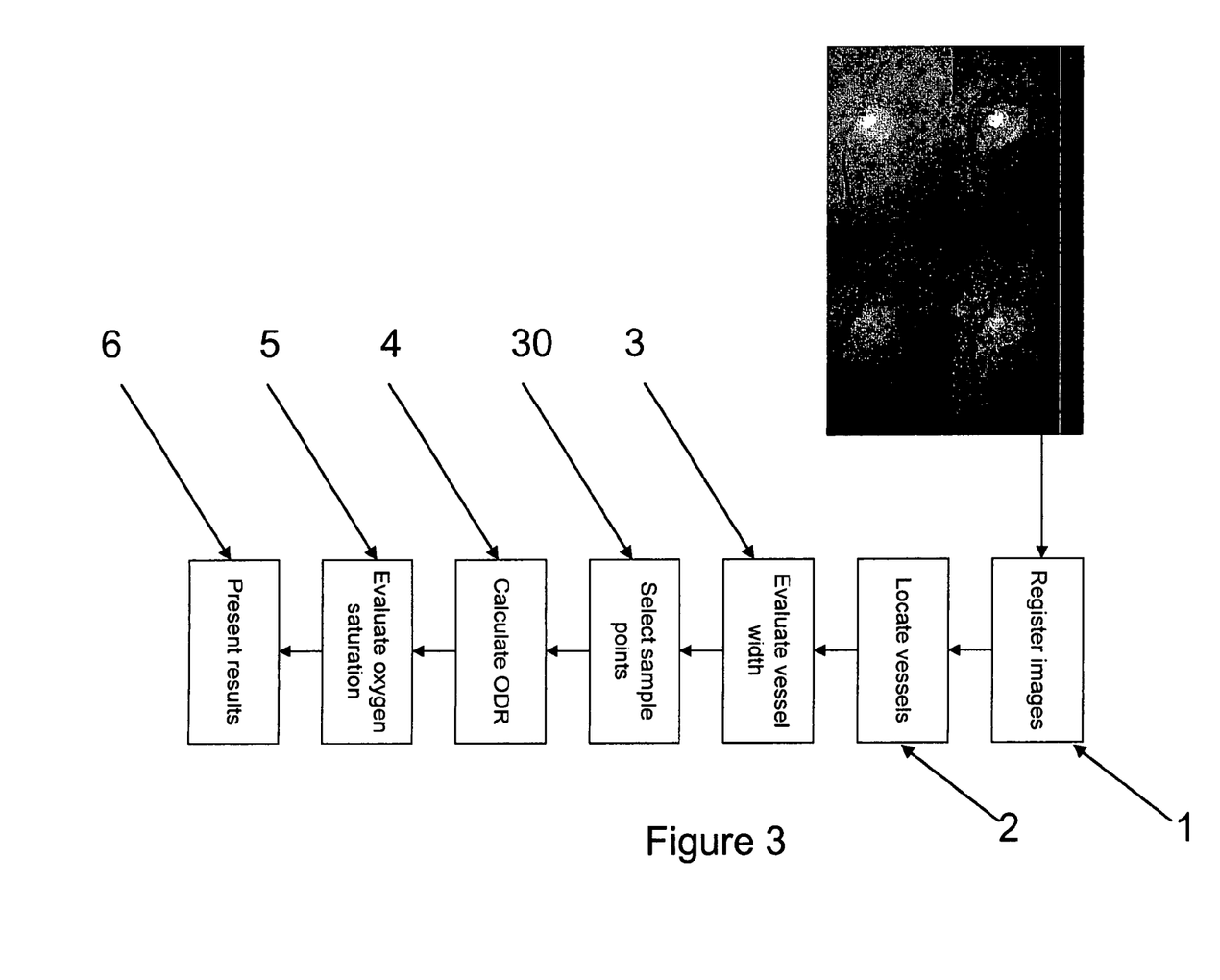
FIG. 3 shows a functional flow graph of the retinal oxymetry process.

FIG. 3 is a flow diagram that illustrates the sequence of events performed by the retinal oximetry software for processing the multi-spectral images.

Figure 4:
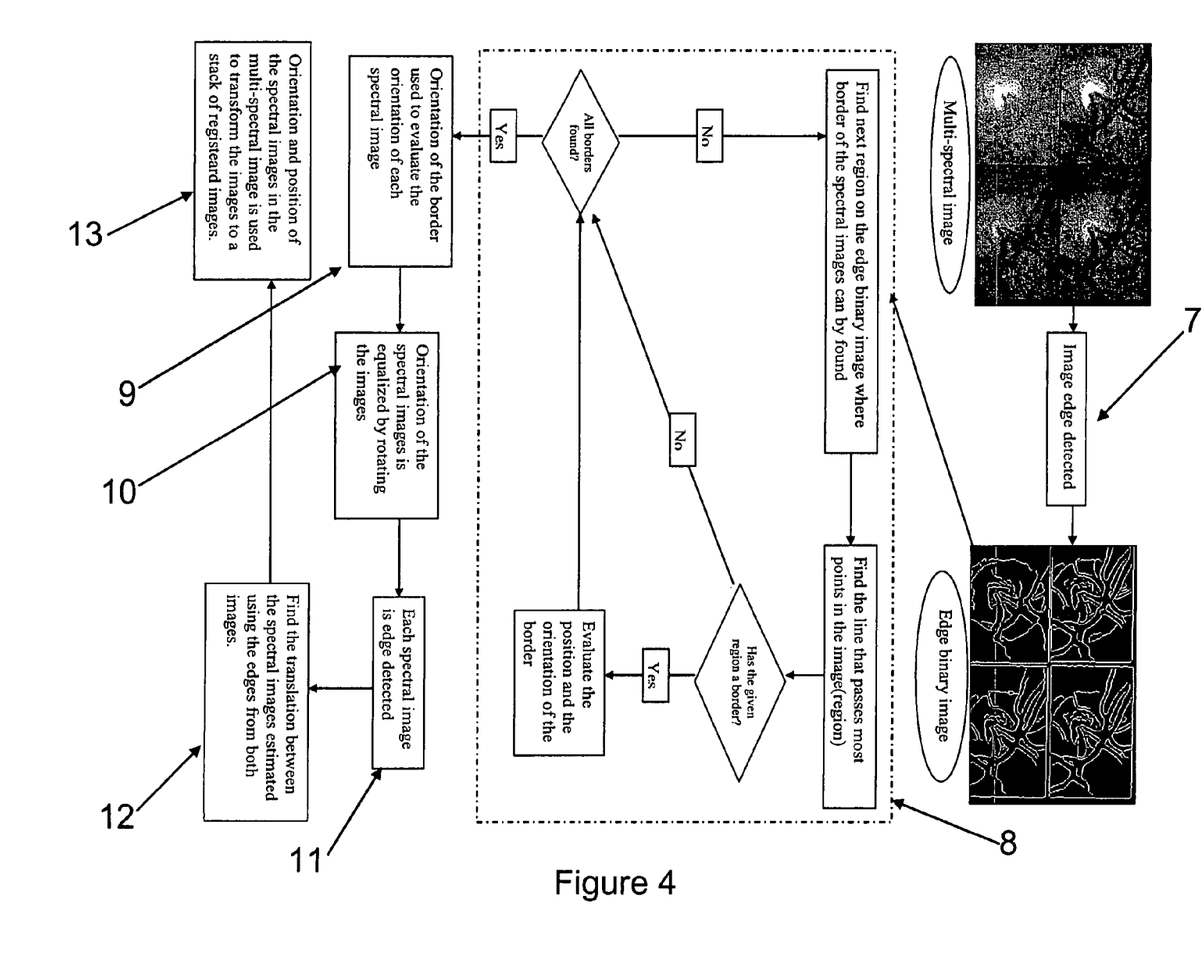
FIG. 4 shows a functional flow graph of the image registration process.
Figure 5:
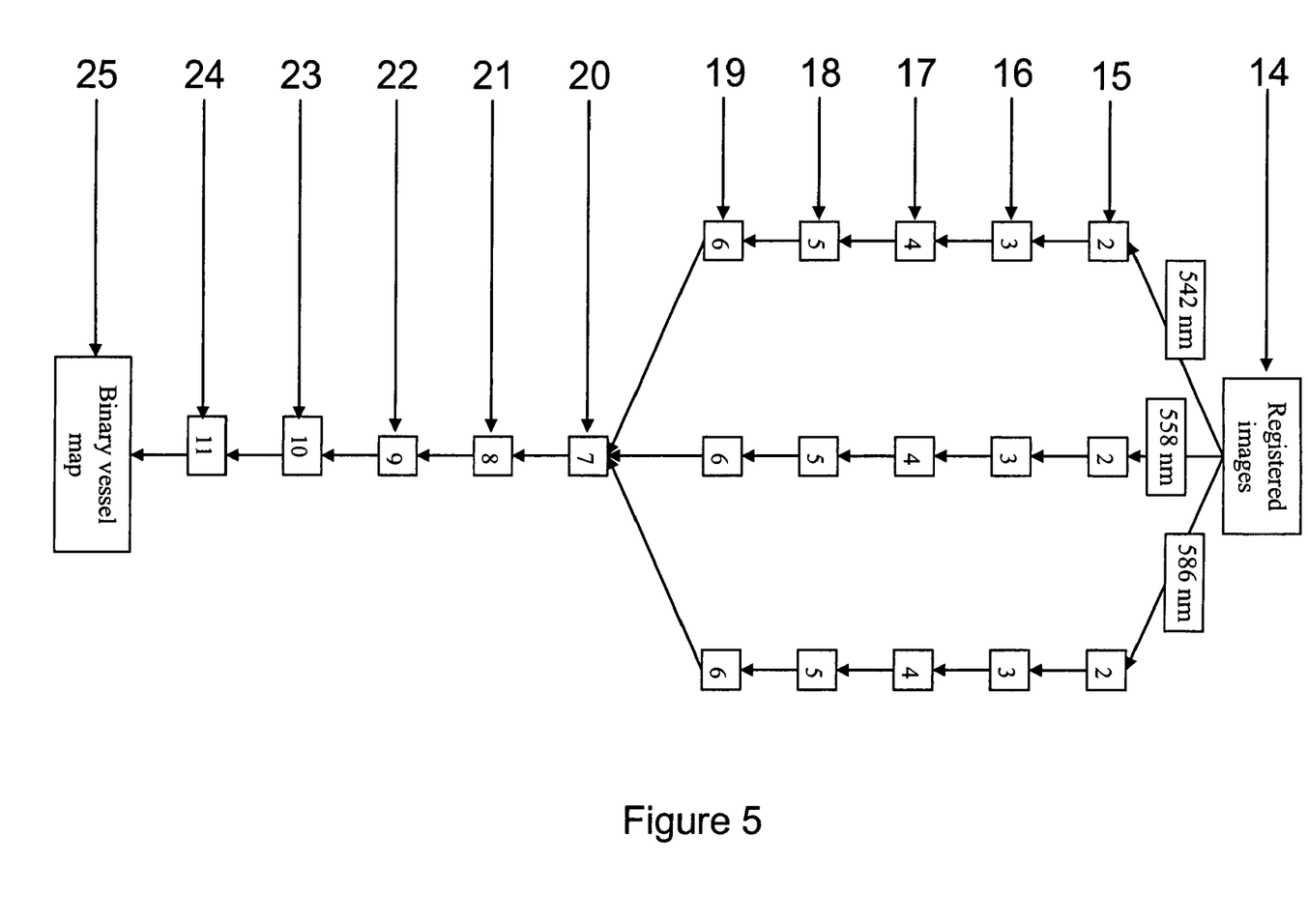
FIG. 5 shows a functional flow graph of the vessel location process.

The first task is preprocessing and registration of the spectral images and includes the following steps as shown in FIG. 4:

Image Edge Detected (7)

Figure 8:
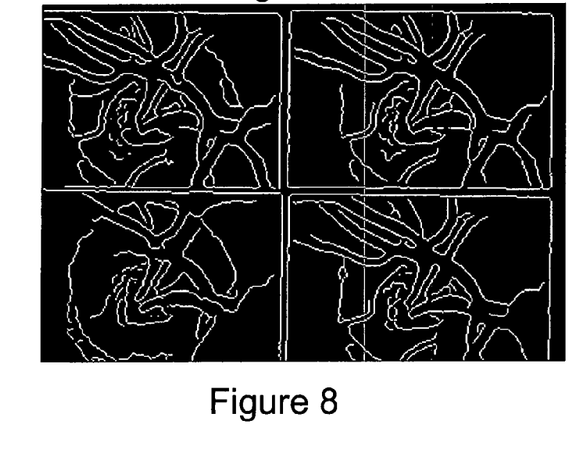
FIG. 8 shows binary edge detected image.

Edge detection is used to extract edges or boundaries between two regions in the image. Common edge detection methods such as Canny or Sobel are used. Mathematically the edges are the gray level gradient of the image and edge detection methods often involve defining the optimum gradient operators. Binary edge detected image, FIG. 8, is derived by thresholding the gradient of the image using for the Canny method.

Evaluate a Border Region (8)

Figure 6:
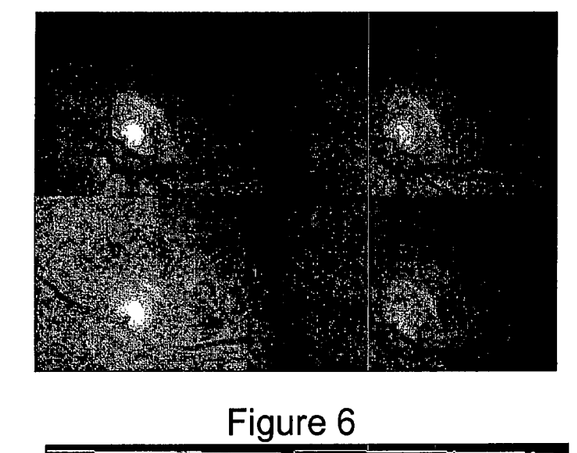
FIG. 6 shows a typical multi-spectral image.
Figure 7:
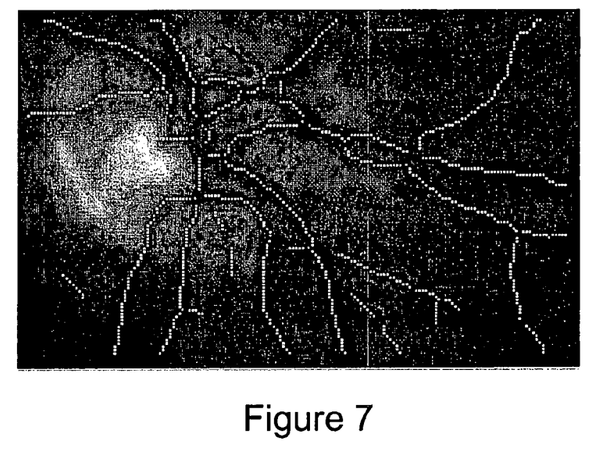
FIG. 7 shows results from the automatic vessel selection.

The multi-spectral image, FIG. 6, contains four spectral images that are always ordered the same way and their position does not change dramatically. The mechanical sensitivity of the device to capture the images does only produce uncertainty in the image position (and rotation), which is no more than ±20 pixels (concluded after examining large amount of data).

Therefore, the area on the multi-spectral image, for finding the border of each spectral image, is evaluated as percent of the multi-spectral image size.

Find the line that passes most points in the image
    The line that passes the most points is found by using the Hough transform. The line is located by transforming the region of the image, and finding the position of the maximum value in the Hough space.
    Has the given region a border?
    The only problem with the uncertainty in the position of the borders is that the spectral images can overlap and borders can be out side the multi-spectral image.
    To evaluate if the region has a border a following methodology is used:
        If the magnitude of the maximum value of the Hough transform is P % of the line length, the line is assumed to be a border.
    To discriminate between two borders that lie close together on the binary edge image the edge gradient direction is used.

Find the Orientation of Each Spectral Image (9)

The orientation of the image can be estimated without using the similarity metric, since each spectral image has at least one visible border on the multi-spectral image. The Hough transformation is used to find how many points lie on lines that have orientation in a particular range. Therefore, the boarder orientation of the spectral images' is estimated by choosing the line that intersects the maximum number of points. Finally, the orientation of each spectral image is calculated using a weighted average of the border orientation, weighting each possible border with how many points the border line intersects.

Equalize the Orientation of the Spectral Images (10)

Position of each border, detected previously is used to cut large region around the spectral image out of the multi-spectral image. Then, the orientation of the spectral images is equalized by rotating each image.

Find the Translation between the Spectral Images (12)

After the images have been rotated for orientation equalization, the translation between them is evaluated. The translation between the spectral images is estimated using the edges from both images. Then, by searching over all translation ((tx,ty)±20), the most likely translation is the one which has the most edges with similar gradient direction and magnitude.

The Second Task is to Detect and Locate the Vessels:

First the registered spectral images are retrieved (14). The images are searched for defective pixels and these pixels are then removed from each of the spectral images (15). Next, each of the spectral images goes through a contrast enhancement process (16) to improve the contrast between the background and the features (vessels) of the images. Thereafter, the images are processed using the Black-Top-Hat transform using a structuring element in the shape of a disk with diameter larger than the diameter of the largest vessel (17). Next, each image is thresholded at for example 80% of the mean pixel value (18). After the thresholding procedure the images a median filter is applied to each of the images to smoothen them (19). After processing each image separately the resulting binarized images are combined by applying a binary AND operation on each pixel in the images (20). The resulting image is then skeletonised to find the centerline of the vessels (21). The skeletonized image is pruned (22), and the resulting image is then re-grown (23) to remove the spurs from the skeletonized image. Finally the junction points (24) of the vessels are located and binary vessel map is produced (25), FIG. 8.

The third task is to evaluate the vessel width and segment length. The binary vessel map is used to evaluate the direction and position of the vessel profile which is a perpendicular normal to the vessel direction. The profile is then used to evaluate accurate position of vessel walls (edges) and calculate the vessel width.

The fourth task is to select the sample points to use for the calculation of the optical density ratio. The points are selected both inside a vessel, to estimate the absorption of the blood and outside the vessels to estimate the amount of light entering the vessel. The points within a vessel are selected by locating the darkest spot within the vessel profile previously obtained and then average the value of the closest eight neighboring pixels within the vessel. The points outside the vessels are selected by moving away from the vessels in a perpendicular direction from the points selected within the vessel until a predetermined distance is reached for example 20 pixels. Again, the pixel values in its 8-connected neighborhood are averaged.

The fifth task is to evaluate the optical density. This is accomplished using following equation were the Light reflected by the background is the average pixel value from background and the Light reflected from vessel is the average pixel value within the selected vessel as described in the previous paragraph.

$$OD = \log\left(\frac{\text{Light reflected by background}}{\text{Light reflected from vessel}}\right)$$

OD is then calculated at each wavelength ($OD_{542\ nm}$, $OD_{558\ nm}$, $OD_{586\ nm}$ and $OD_{605\ nm}$), and finally the optical density ratio at two different wavelengths is calculated $$ODR = \frac{OD_X}{OD_Y}$$

The sixth task is to evaluate the oxygen saturation of the blood. As previously described, by selecting appropriate wavelengths when calculating this ratio (Y=586 nm and X={542,558,605}nm), a linear relationship exists between ODR and the oxygen saturation in the retinal vasculature, which in turn makes it possible to estimate the oxygen saturation.

The final step is to present the results. After the software has calculated OD values for each wavelength the optical density ratio (ODR) is calculated using one isobestic wavelength and one non-isobestic wavelength. The ODR information for any venule or arteriole is represented as numerical and visual information on the computer screen and stored in a data file for further investigation.

Vessel Classification

In order to measure automatically the difference between the oxygen content of the blood flowing to the retina of the eye and the blood going from it, the ability to classify the detected vessels as either arterioles or venules is quite important. In our software, a positive definite fuzzy classifier [9] is applied to the data collected by the vessel location method. Each pixel belonging to a vessel, as determined by the vessel classification algorithm, is classified as either a pixel belonging to a venule or an arteriole. In order to adjust for variability in illumination between images the input variables are scaled using the mean pixel value of its respective spectral band. The vessel itself is then classified according to which class the majority of the pixels within it are determined to belong to (see results in FIG. 4).

Experimental Results:

The software has been used to examine reproducibility and sensitivity of ODRs for different oxygen tensions. The results are given below.

Reproducibility:

Reproducibility was evaluated by measuring the same vessel on five consecutive images. Coefficient of variation (CV) was calculated as $$CV = \frac{\text{Standard deviation of } ODR \text{ (5 images of the same vessel)}}{\text{Mean } ODR \text{ (5 images of the same vessel)}}\left(1 + \frac{1}{4n}\right)$$

where n=5 measurements (images). One arteriole and one venule were measured in images from 11 eyes. The CV was calculated for measurements with both the automatic version of the software and with an older version of the software, which allows only manual placement of measurement points. The results are shown in Table 1.

TABLE 1

CV for automatic and manual software

| | Arterioles | | Venules | |
|---|---|---|---|---|
| | Manual | Automatic | Manual | Automatic |
| CV (mean, range) | 48% (15-139%) | 16% (8-26%) | 19% (5-81%) | 8% (3-16%) |

As seen in Table 1, the automatic approach to point selection clearly increases the reproducibility.

Sensitivity:

Sensitivity of the system was evaluated by comparing ODRs in arterioles and venules and by measuring changes in ODRs (or venular oxygen saturation) when healthy volunteers inhaled different concentration of oxygen.

Figure 9:
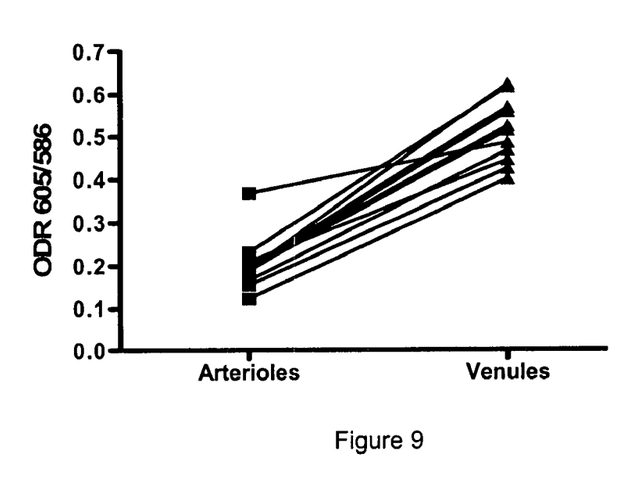
FIG. 9 shows results for arterioles and venules measured at 21% $O_2$. Each line represents one eye. Paired t-test, arterioles vs. venules: p<0.0001

FIG. 9 shows ODRs for arterioles and venules (subjects inhaling room air).

FIG. 9. Arterioles and venules measured at 21% $O_2$ Each line represents one eye. Paired t-test, arterioles vs. venules: p<0.0001.

FIG. 9 shows that the system is sensitive to the arteriovenous difference in ODRs (and therefore to the a.-v. difference in oxygenation). Furthermore, the size of the arteriovenous difference is similar between most individuals although the offset (arteriolar ODR) is variable.

Since oxygen tension in the retinal arterioles can be assumed to be similar to oxygen tension in arterial blood elsewhere in the body, calibration whith a commercially available finger pulse oximeter is possible. This calibration would almost eliminate the intersubject variability in the arterioles in FIG. 9. Assuming a linear relationship between ODR and hemoglobin oxygen saturation ($S_{o_2}$) and using finger oximetry values for retinal arterioles we found that $\Delta S_{o_2}= -89\Delta ODR$ (preliminary result, 95% confidence interval for the slope is −125 to −53). This calibration was done with data from experiments where healthy volunteers inhaled either 12%, 21% or 100% oxygen to induce systemic hypoxia, normoxia and hyperoxia, respectively.

Figure 10:
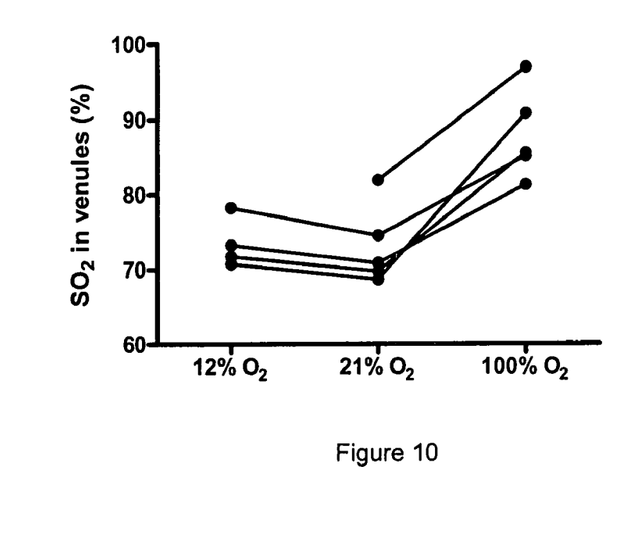
FIG. 10 shows results for venules measured at different $O_2$ concentration in inhaled air. Paired t-test, 21% vs. 100%: p=0.0023.

FIG. 10 shows the results from the hypoxia-normoxia-hyperoxia experiments for venules. One point from the hypoxia part of the experiment was omitted because the subject was not rendered hypoxic according to the finger pulse oximeter.

FIG. 10. Venules measured at different $O_2$ concentration in inhaled air. Paired t-test, 21% vs. 100%: p=0.0023.

The reason for the lack of difference between results for 12% and 21% inhaled oxygen concentration is most likely the well-known phenomenon of blood flow autoregulation [14]. When the oxygen concentration in arteriolar blood decreases the arterioles dilate, blood flow increases and similar amount of oxygen is delivered to the tissue. Therefore, there is little or no change in venular oxygen tension. On the other hand, the system detects a significant difference in the venules when inhaled oxygen tension is changed from 21% to 100% (see FIG. 10). This is probably due to the effects of the choroid, which is a non-autoregulated vascular bed underneath the retina. ODRs are measured in the visible vasculature which nourishes the inner part of the retina. The choroid does not usually deliver oxygen to the inner part of the retina [14]. However, when 100% oxygen is inhaled, some of the oxygen will diffuse to the inner retina and this probably overwhelmes the autoregulation of blood flow in the inner vasculature.

In summary, the results show that the system can detect expected differences in venular oxygenation when oxygen concentration in inhaled air is altered. Autoregulation of blood flow most likely explains part of the results.

REFERENCES

1. Tiedeman, J. S., et al., "Retinal oxygen consumption during hyperglycemia in patients with diabetes without retinopathy," Ophthalmology, 1998. 105(1): p. 31-36.
2. Beach, J. M., et al., "Oximetry of retinal vessels by dual-wavelength imaging: calibration and influence of pigmentation," J Appl Physiol, 1999. 86(2): p. 748-58.
3. Delori, F. C., "Noninvasive techniques for oximetry of blood in retinal vessels," Applied Optics, 1988. 27: p. 1113-1125.
4. Crittin, M., H. Schmidt, and C. E. Riva, "Hemoglobin oxygen saturation (So2) in the human ocular fundus measured by reflectance oximetry: preliminary data in retinal veins," Klin Monatsbl Augenheilkd, 2002. 219(4): p. 289-91.
5. Beach, J. M. "Spectral Reflectance Technique for Retinal Blood Oxygen Evaluation in Humans," in Applied Imagery Pattern Recognition Workshop Proceedings. 2002: IEEE.
6. Ashman, R. A., F. Reinholz, and R. H. Eikelboom, "Oximetry with a multiple wavelength SLO," Int Ophthalmol, 2001. 23(4-6): p. 343-6.
7. Halldorsson, G. H., et al. "Automatic Registration of Spectrophotometric Retinal Images," in 2004 IEEE Nordic Signal Processing Workshop (NORSIG 2004). 2004. Helsinki.
8. Karlsson, R. A., et al., "Automatic selection of measurement points in multispectral fundus images for retinal oximetry," Invest Ophthalmol, 2003. 45 (E-abstract 3016).
9. Chen, Y. and J. Z. Wang, "Support vector learning for fuzzy rule-based classification systems," IEEE Transactions on Fuzzy Systems, 2003. 11(6): p. 716-728.
10. Bouzas, E. A., G. Donati, and C. J. Pournaras, "Distribution and regulation of the optic nerve head tissue PO2," Surv Ophthalmol, 1997. 42 Suppl 1: p. S27-34.
11. Delaey, C. and J. Van De Voorde, "Regulatory mechanisms in the retinal and choroidal circulation," Ophthalmic Res, 2000. 32(6): p. 249-56.
12. F. Meyer, "Contrast feature extraction," in Quantitative Analysis of Microstructures in Material Sciences, Biology and Medicine, (J.-L. Chermant, ed.), (Stuttgart, FRG), Riederer Verlag, 1978. Special issue of Practical Metallography.
13. A. Harris, R. B. Dinn, L. Kagemann and E. Rechtman, "A review of methods for human retinal oximetry," Ophthalmic Surg Lasers Imaging. March-April; 34(2):152-64, 2003.
14. Delaey, C. and J. Van De Voorde, "Regulatory mechanisms in the retinal and choroidal circulation." *Ophthalmic Res* 32(6): 249-56, 2000.

The invention claimed is:

1. A method implemented by a computer-based imaging system for evaluating oxygen saturation of optic nerve and retina, said method comprising:
   registering a set of spectral images of a retina within a multi-spectral image, which comprises
   using border regions to estimate orientation of each spectral image,
   equalizing the orientation of each spectral image by rotating the spectral image, edge-detecting each spectral image,
estimating a translation between the spectral images based on the edges of adjacent spectral images, and
transforming the spectral images to a stack of registered spectral images,
locating blood vessels in each of the spectral images,
evaluating a width of the blood vessels,
selecting sample points for calculating optical density,
calculating an optical density ratio, wherein the optical density is a logarithm of light reflected from background divided by light reflected from the blood vessel and said optical density ratio is ratio of said optical density at two different wavelengths,
evaluating oxygen saturation level, and
presenting results to indicate the oxygen saturation level of the optic nerve and retina.

2. The method of claim 1, wherein said presenting of results includes presenting numerical and/or visual representation of the oxygen saturation level.

3. The method of claim 1, wherein said using border regions to estimate the orientation of each spectral image further comprises:
edge detecting the multi-spectral image,
locating a limited region of the multi-spectral image where a border of the spectral image is likely to be found,
inside the limited region, finding a straight line that passes the most number of pixels in the edge detected spectral image, and
using the orientation of the lines to evaluate the orientation of each spectral image.

4. The method of claim 1, wherein said locating blood vessels further comprises:
retrieving registered spectral images,
for each spectral image,
removing defective pixels,
enhancing image contrast,
performing top-hat transform using structuring element larger than the largest blood vessel diameter,
binarizing each spectral image,
applying spatial filter for smoothing the spectral image,
combining all the spectral images using binary AND operator,
skeletonizing the resulting spectral image,
pruning the skeleton spectral image,
re-growing the pruned spectral image, and
locating junction points,
wherein the junction points are the intersection of two or more blood vessels.

5. The method of claim 1, wherein said evaluating the width of the blood vessels further comprises:
evaluating binary vessel map by calculating a normal vector of the blood vessel direction to estimate the direction and position of blood vessel profile,
evaluating positions of blood vessel walls based on the blood vessel profile obtained, and
evaluating blood vessel width based on the position of the blood vessel walls,
wherein the width is a distance between the blood vessel walls.

6. The method of claim 1, wherein said selecting sample points for calculating optical density comprises selecting sample points within the blood vessel and outside the blood vessel, said selecting the sample points includes:
locating a spot within the blood vessel profile previously obtained, with lowest magnitude,
averaging value of a predetermined number of symmetrically neighboring pixels, and
moving away from the blood vessel in a predetermined distance and, with a provision that the location not being inside another blood vessel, averaging a value of a predetermined number of symmetrically neighboring pixels.

7. A method implemented by a computer-based imaging system for automatic registration of spectral images within a multi-spectral image, said method comprising:
using border regions to estimate orientation of each spectral image by:
edge detecting the spectral image,
locating a limited region of the spectral image where a border of the spectral image is likely to be found,
inside the limited region, finding a straight line that passes the most number of edge detected pixels, and
using the orientation of the lines to evaluate the orientation of each spectral image,
equalizing the orientation of each spectral image by rotating the spectral image,
edge detecting each spectral image,
estimating a translation between the spectral images based on the edges of adjacent spectral images, and
transforming the spectral images to a stack of registered spectral images,
wherein the spectral images are transformed based on orientation and position of each spectral image.

8. A system for automatically evaluating oxygen saturation of optic nerve and retina, said system comprising:
an image capturing system, comprising:
a fundus camera,
a four wavelengths beam splitter,
a digital image capturing device, and
a computer system configured to perform in real-time the method of claim 1.

9. The system of claim 8, wherein said computer system is further configured for presenting results indicating oxygen saturation having presentation of numerical and/or visual representation of the oxygen saturation.

10. The system of claim 8, wherein said computer system is further configured to register a set of spectral images within a multi-spectral image through steps comprising:
edge detecting the spectral image,
locating a limited region of the spectral image where a border of the spectral image is likely to be found,
inside the limited region, finding a straight line that passes the most number of edge detected pixels,
using the orientation of the lines to evaluate the orientation of each spectral image,
equalizing the orientation of each spectral image by rotating the spectral image,
edge-detecting each spectral image,
estimating a translation between the spectral images based on the edges of adjacent images, and
transforming the spectral images to a stack of registered spectral images,
wherein the spectral images are transformed based on orientation and position of each spectral image.

11. The system of claim 8, wherein said computer system is further configured to locate blood vessels in each of the multi-spectral images by steps comprising:
retrieving registered spectral images,
for each spectral image,
removing defective pixels,
enhancing image contrast, performing top-hat transform using structuring element larger than largest blood vessel diameter,
binarizing each spectral image, and
applying filter for smoothing the spectral image,
combining all the spectral images using binary AND operator,
skeletonizing the resulting spectral image,
pruning the skeleton spectral image,
re-growing the pruned spectral image,
locating junction points, and
wherein the junction points are the intersection of two or more blood vessels.

12. The system of claim 8, wherein said computer system is further configured to evaluate the width of said blood vessels by steps comprising:
estimating the direction and position of the blood vessel profile,
evaluating positions of blood vessel walls based on the blood vessel profile obtained,
evaluating blood vessel width based on the position of the blood vessel walls,
wherein the width is the distance between the blood vessel walls.

* * * * *